United States Patent [19]
Wang et al.

[11] Patent Number: 5,999,834
[45] Date of Patent: Dec. 7, 1999

[54] DISPOSABLE ADHESIVE WRAP FOR USE WITH REUSABLE PULSE OXIMETRY SENSOR AND METHOD OF MAKING

[75] Inventors: Huisun Wang, Hamden; Kimberley A. Golden, Wallingford, both of Conn.

[73] Assignee: NTC Technology, Inc., Wilmington, Del.

[21] Appl. No.: 09/099,833

[22] Filed: Jun. 18, 1998

[51] Int. Cl.⁶ ...................................................... A61B 5/00
[52] U.S. Cl. ............................................ 600/344; 600/310
[58] Field of Search .................................. 600/310, 322, 600/323, 340, 364

[56] References Cited

U.S. PATENT DOCUMENTS

| | | |
|---|---|---|
| 4,685,464 | 8/1987 | Goldberger et al. . |
| 4,825,879 | 5/1989 | Tan et al. . |
| 4,830,014 | 5/1989 | Goodman et al. . |
| 4,865,038 | 9/1989 | Rich et al. . |
| 4,928,691 | 5/1990 | Nicolson et al. . |
| 5,109,849 | 5/1992 | Goodman et al. . |
| 5,170,786 | 12/1992 | Thomas et al. . |
| 5,209,230 | 5/1993 | Swedlow et al. . |
| 5,217,012 | 6/1993 | Young et al. . |
| 5,337,744 | 8/1994 | Branigan . |
| 5,438,986 | 8/1995 | Disch et al. . |
| 5,469,845 | 11/1995 | DeLonzor et al. . |
| 5,830,136 | 11/1998 | Delonzor et al. ..................... 600/344 |

Primary Examiner—Eric F. Winakur
Attorney, Agent, or Firm—Trask, Britt & Rossa

[57] ABSTRACT

An oximetry sensor comprising a wrap member including a fastener and adhesive member and an LED assembly and photodiode connected to a cable.

29 Claims, 7 Drawing Sheets

DISPOSABLE ADHESIVE WRAP FOR USE WITH REUSABLE PULSE OXIMETRY SENSOR AND METHOD OF MAKING

BACKGROUND OF THE INVENTION

1. Field of the Invention

The present invention is related to sensors applied to the body for monitoring or making measurements of body tissue conditions, metabolism or other body functions indicative of health. More specifically, the present invention is directed to a pulse oximetry sensor which can be readily attached and reattached to a portion of the body in a non-invasive manner having an adhesive wrap member for use with a reusable pulse oximetry sensor to retain the sensor in the desired position comfortably on a patient.

2. State of the Art

In the prior art, a non-invasive pulse oximetry sensor may be used to measure the relative oxygen saturation of the blood. Typically, in such prior art types of oximetry sensors, a light source, such as a light emitting diode (LED) is used to alternately direct light of two different wave lengths, such as red and infrared light, to the blood through the skin. The light transmitted or reflected by the blood at the different wave lengths can then be compared to provide a measurement of oxygen saturation of the blood.

A typical prior art probe system contains the light emitting sources, such as the LED's, and a light detector, such as a photodiode, mounted on the appendage of the body, such as a finger, toe, ear lobe, nose, hand, tongue or foot. However, such devices need to be capable of being readily attached to the body appendages, comfortable when attached to a patient, be reusable on the same patient, be relatively inexpensive to manufacture, remain in the desired position on the patient during use without substantial movement, and fit a wide variety of patients without discomfort.

One type of prior art type oximetry sensor uses the mechanical clamping action of spring biased jaws to retain the sensor on an appendage of a patient. Such a device is illustrated in U.S. Pat. Nos. 4,685,464 and 5,438,986. While such devices are effective, they are inherently difficult to clean and inappropriate for the long term use or application on a patient and can only be used on the fingers of a patient. The clamping pressure of the spring biased jaws necessary to maintain the oximetry sensor in position on the patient's finger often is uncomfortable during long-term usage.

Another type of oximetry sensor relies upon a deformable member being located in the device to retain the sensor on the appendage of a patient. Such a device is illustrated in U.S. Pat. Nos. 4,865,038, 4,928,691, and 5,217,012. During the reuse of such sensors on a patient, since the retaining member has been deformed and has a memory, reinstallation of the sensor may affect the comfort of the patient.

In yet another type of oximetry sensor, in an effort to facilitate reuse of the sensor and to provide comfort to the patient during use of the sensor, the sensor is retained on the finger of a patient through the use of hook and loop fabric. However, such sensors have used complex shapes of hook and loop fabric as retaining devices, thereby causing the manufacturing expense of the device to increase. Also, the sensors may need to be installed tightly on an appendage to prevent movement, thereby causing discomfort for the patient. Such sensors are illustrated in U.S. Pat. Nos. 4,825,879, 5,209,230, and 5,469,845.

In another type of oximetry sensor with an adhesive, the adhesive is used to attach the sensor to a patient in an attempt to lower manufacturing cost of the sensor, provide comfort to the patient during use of the sensor, and provide a secure attachment of the sensor to the patient. However, since the device must be often repositioned on a patient, the adhesive loses its adhesive quality during reuse, thereby allowing movement of the sensor. Also, the adhesive may irritate the patient during use, thereby causing discomfort. Such sensors are illustrated in U.S. Pat. Nos. 4,830,014 and 5,170,786.

In yet another type of oximetry sensor, an elastomeric member is used to retain the sensor on the finger of a patient. Although this allows reuse of the sensor, the degree of pressure applied by the elastomeric member and the elastomeric member being in contact with the skin may cause discomfort to a patient and, if too weak, may allow movement of the sensor during use. Such a sensor is illustrated in U.S. Pat. No. 5,337,744.

Since the prior art sensors are generally either reusable and expensive to manufacture, or are not easily reusable and have a relatively low manufacturing cost, or reusable and cause discomfort to the patient, there is a need for a readily positioned, comfortable, extended life, reusable, disposable attachment piece, low manufacturing cost pulse oximetry sensor.

SUMMARY OF THE INVENTION

The present invention is directed to a readily positioned, comfortable, extended life, reusable sensor having a disposable wrap member and low manufacturing cost pulse oximetry sensor. The present invention is also directed to the method of making such an oximetry sensor The oximetry sensor of the present invention comprises a wrap member including a fastener and adhesive member, an LED assembly, and photodiode connected to a cable.

The oximetry sensor and the method of manufacture of the present invention will be better understood when the drawings are taken in conjunction with the description of the invention.

DESCRIPTION OF THE INVENTION

Figure 1:
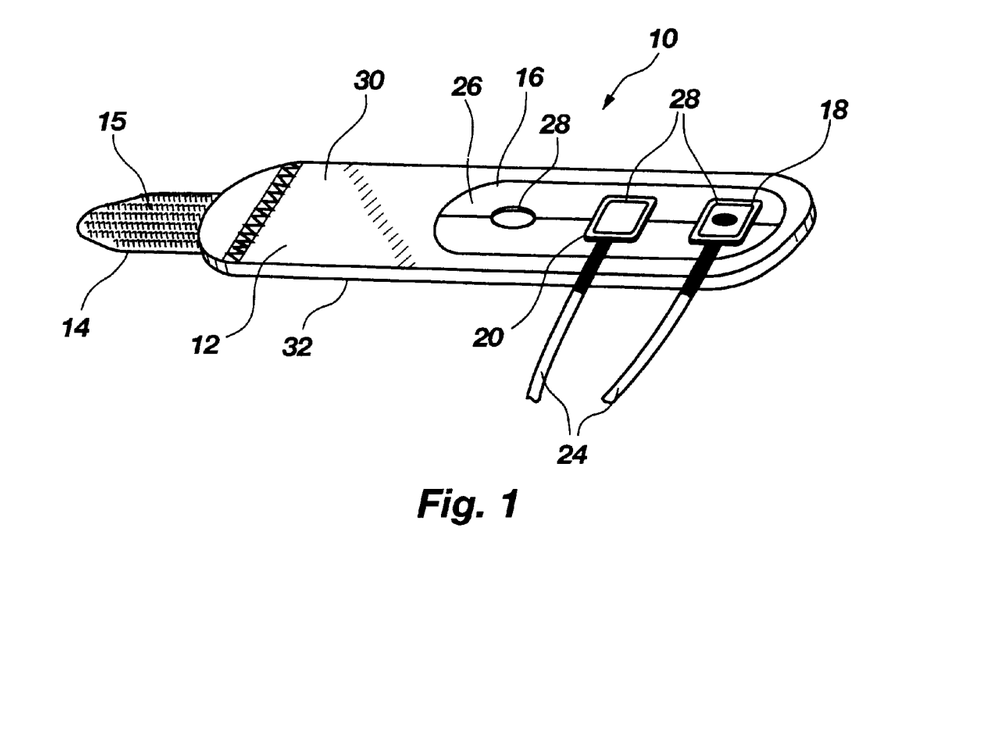
FIG. 1 is a view of a portion of the oximetry sensor of the present invention.

Referring to drawing FIG. 1, the oximetry sensor 10 of the present invention is shown. The oximetry sensor of the present invention comprises a wrap member 12 including a fastener 14, adhesive member 16 initially having a cover 26, a release liner, thereover, LED assembly 18, and photodiode 20 connected to a cable 22.

The wrap member 12 comprises foam lamination having a fabric cover thereover and a fastener 14 attached thereto and a plurality of apertures 28 formed therein to retain portions of the LED assembly 18 and photodiode 20 therein. The foam portion 30 of the wrap member 12 comprises any suitable type foam, such as a polyester foam, or any suitable compliant substrate, foam substrate, comfortable foam substrate, or plastic foam, substrate as the foam member. The fabric portion 32 of wrap member 12 comprises any suitable fabric, such as a fabric having a plurality of loops integrally formed therein, which may be readily engaged by a plurality of fastening members located on the fastener 14 of the wrap member 12. The fastener 14 attached to the wrap member 12 comprises a molded plastic member having a plurality of hooks 15 formed on one surface thereof to engage the plurality of loops formed in the fabric portion 32 of the wrap member 12. The combination of the fastener 14 having a plurality of hooks 15 formed on one surface thereof and the fabric portion 32 of the wrap member 12 is commonly referred to as a VELCRO type fastener comprised of synthetic materials which adhere when pressed together. The foam portion 30 and fabric portion 32 of the wrap member 12 are secured together by any suitable means of fastening, such as adhesive bonding. The fastener 14 of the wrap member 12 is secured to the foam portion 30 and fabric portion 32 of the wrap member 12 by any suitable means, such as adhesive bonding, sewing, ultrasonic staking, the natural tendencies of these materials to adhere to each other, etc.

The adhesive member 16 located on the wrap member 12 may be any suitable type, such as a double-sided adhesive tape coated with a suitable adhesive, one side of the member 16 being adhesively secured to the wrap member 12 while the other side thereof initially has a paper, or other suitable material, covering 26, a release liner, releasably retained thereover which is removed for installation of the oximetry sensor 10 of the present invention on a patient. As shown, the adhesive member 16 is a generally rectangular shaped member secured to the wrap member 12. If desired, the adhesive member 16 may be of any other suitable shapes, such as an annular member, etc. The adhesive member 16 is used to retain the oximetry sensor 10 of the present invention in position on a patient while the fastener 14 retains the sensor 10 on the patient. Alternately, rather than using a double-sided adhesive member 16, the member 16 may be a soft, compliant elastomeric member, such as a silicon elastomeric member, having an adhesive coating on one side thereof to retain the member 16 on the wrap member 12 with the friction of the soft elastomeric member against the skin of a patient being sufficient to retain the wrap member 12 in position without requiring the wrap member 12 to be tightly wrapped about the patient's finger or the like causing discomfort.

The LED assembly 18 includes a red light emitting diode and an infrared light emitting diode adjacently mounted, forming a rectangular shaped member. As is known in oximetry, the transmission of light in the red range of the spectrum, i.e., at a wave length of approximately 660 nanometers, through blood is substantially affected by the amount of oxygenated hemoglobin present in the blood. The transmission of light in the infrared range of the spectrum, i.e., at a wave length of approximately 940 nanometers, through blood is substantially unaffected by the amount of oxygenated hemoglobin present in the blood. Oximeters use this principle to alternately illuminate the blood through the tissue with light of the foregoing respective wave lengths. The LED assembly 18 includes a base (not shown) which engages an opening 28 in the wrap member 12 to resiliently retain the assembly 18 therein.

The photodiode 20 is sensitive to red light and infrared light. The photodiode 20 alternately senses radiated red and infrared energy. The photodiode 20 includes a base (not shown) which engages an aperture 28 in the wrap member 12 to resiliently retain the photodiode 20 therein.

The cable 22 (FIG. 2) is connected to the LED assembly 18 and photodiode 20 via suitable wire connections 24 thereto. The cable 22 includes a suitable connector 40 (not shown) on the end thereof for connecting the LED assembly 18 and photodiode 20 to a suitable display. Alternatively, the LED assembly 18 and photodiode 20 may be connected to a suitable device through the use of a flexible printed circuit or the like.

Figure 1A:
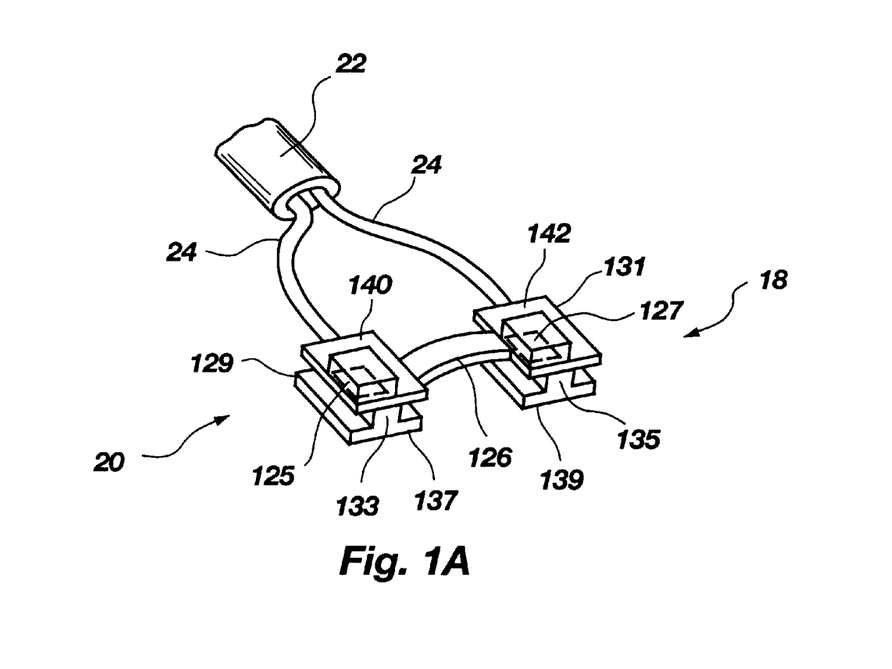
FIG. 1A is an enlarged view of the LED assembly, photodiode, and portion of the connecting cable of the present invention.

Referring to drawing FIG. 1A, the photodiode 20 includes housing 125 which is in the shape of a geometric rectangular solid, one face of which is framed by an integral rectangular flange 129. Similarly, the LED assembly 18 includes housing 127 which is in the shape of a geometric rectangular solid, one face of which is framed by an integral rectangular flange 131. The housings 125 and 127 are interconnected by connecting member 126 and preferably formed from a soft, pliant, rubber-like material include projections 133 and 135 therefrom which include flanges 137 and 139, respectively, which are received in apertures 28 of the adhesive wrap member 12 to releasably retain the photodiode 20 and LED assembly 18 therein. The flanges 137 and 139 may be of any suitable shape, such as rectangular, circular, elliptical, ovoid, etc. Similarly, the housings 125 and 129 may be of any suitable shape, such as rectangular, circular, etc. The flanges 129 and 131 of housings 125 and 127, respectively, include coverings 140 and 142 thereover having a window portion therein to allow infrared light from the LED assembly 18 to be visible and transmitted therethrough to be detected by the photodiode 20. Cable 22 includes wires 24 connected to the photodiode 20 and LED assembly 18.

Figure 2:
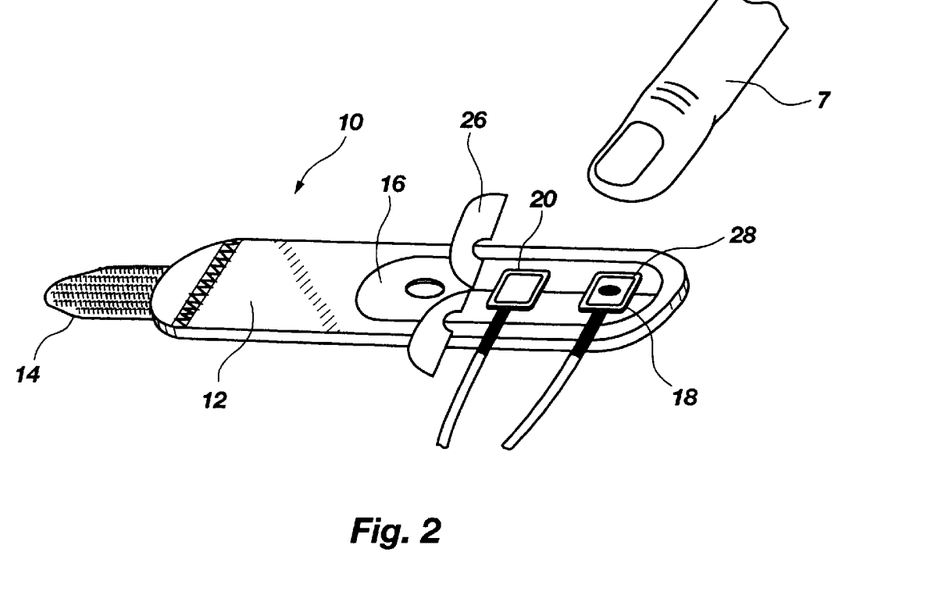
FIG. 2 is a view of the oximetry sensor of the present invention in relation to the finger of a patient before the oximetry sensor is installed thereon.

Referring to drawing FIG. 2, the oximetry sensor 10 of the present invention is shown in relation to the finger 7 of a patient before the installation thereon. As shown, the oximetry sensor 10 comprises a generally elongated rectangular shaped wrap member 12 which is initially disposed generally perpendicularly to the finger 7 of a patient before the installation thereon. The LED assembly 18 and photodiode 20 are generally arranged to be located on opposite sides of the patient's finger 7 when the pulse oximetry sensor is installed thereon. The pulse oximetry sensor 10 of the present invention may be used on other sites of a patient, such the heel, etc., depending upon the desired point of application. Before the installation of the oximetry sensor 10 on the finger of a patient, the paper covering 26 is removed from the adhesive member 16 so that the adhesive member 16 will prevent substantial movement of the wrap member 12 on the finger 7 of a patient after the wrapping of the wrap member 12 therearound. When the LED assembly 18 and photodiode 20 are installed on the wrap member 12, the connecting member 126 is removed therefrom.

Figure 3:
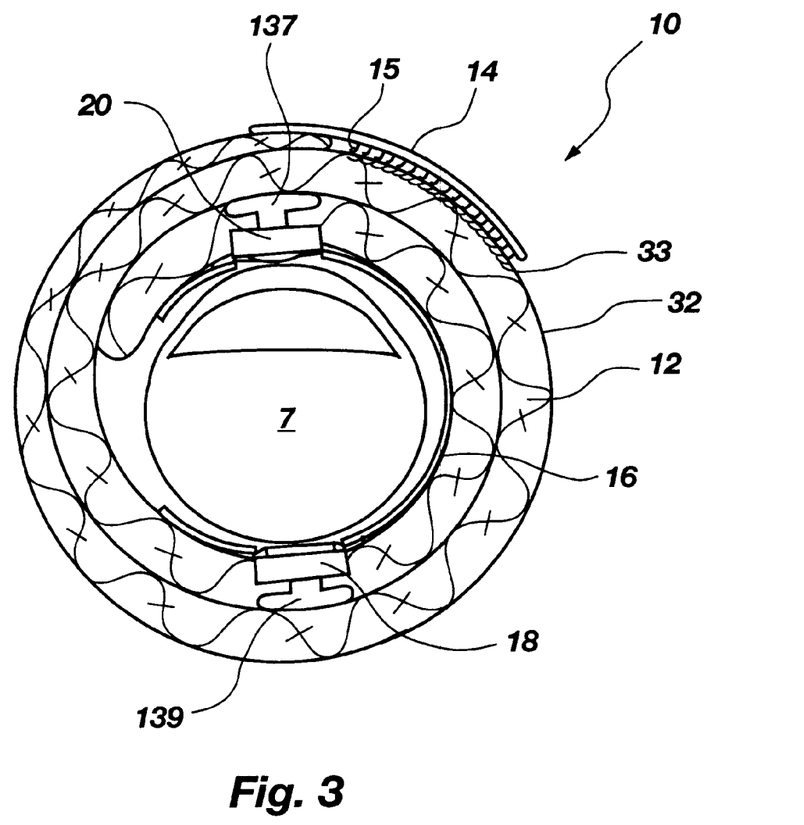
FIG. 3 is a view of the oximetry sensor of the present invention installed on the finger of a patient.

Referring to drawing FIG. 3, the oximetry sensor 10 is shown installed on the finger 7 of a patient. As installed, the oximetry sensor 10 is wrapped around the finger 7 of a patient so that the LED assembly 18 is located generally opposite the photodiode 20 in engagement with the skin and/or the fingernail of the finger 7 with the adhesive member 16 in contact with the finger 7. In this manner, the red and infrared light emitted from the LED assembly 18 is transmitted through the tissue of the finger 7 and detected by the photodiode 20. The wrap member 12 of the oximetry sensor 10 is generally wound around the finger 7 so that the fastener 14 having hooks 15 thereon of the wrap member 12 releasably engages the loops 33 of the fabric portion 32 of the wrap member 12. To adjust the oximetry sensor 10 on the finger 7 of a patient, since the wrap member 12 is compressible and conformable, the wrap member 12 may be rotated around the finger 7 without unfastening or the fastener 14 being disengaged or removed from engaging the fabric portion 32 of the wrap member 12 and the wrap member 12 unwrapped from engaging the finger 7. Since the wrap member 12 is compressible and conformable, the amount of force caused by the wrapping of the oximetry sensor 10 around the finger 7 may be adjusted and controlled to provide the desired amount of force during use without causing discomfort or trauma to the finger 7 of a patient. Additionally, since the fastener 14 may be engaged with the fabric portion 32 of the wrap member for repeated installation, adjustment, and removal of the sensor 10 from the finger 7 of a patient, the oximetry sensor 10 can be repeatedly reused on the same patient without any substantial loss of fastening ability. Furthermore, the adhesive member 16 does not adhere to the finger 7 to prevent the ready positioning of the wrap member 12 on a patient.

Figure 4:
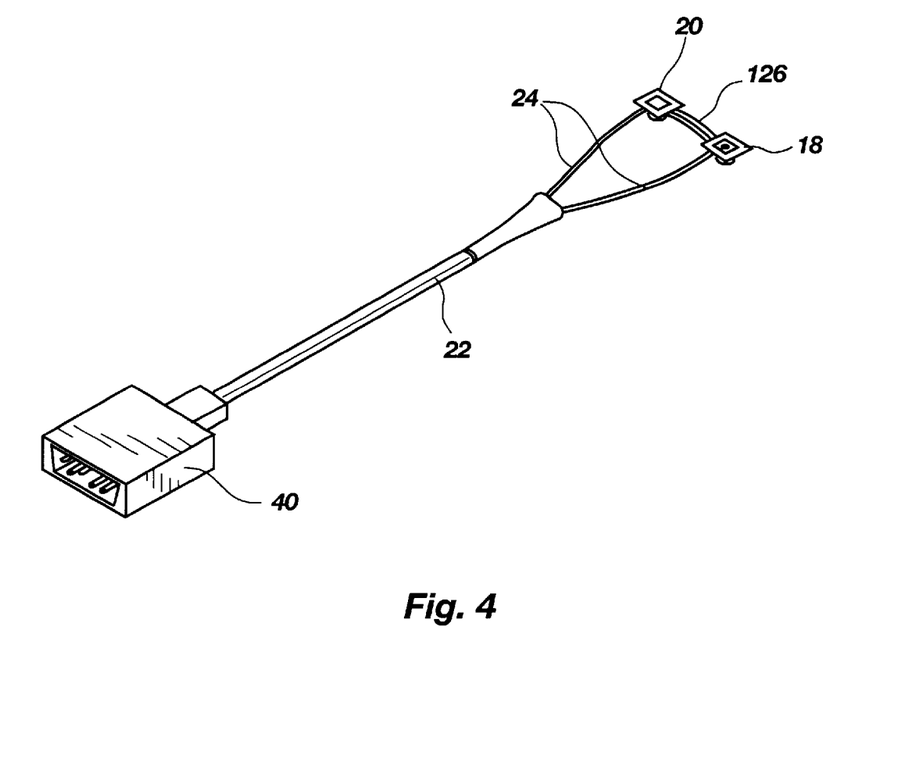
FIG. 4 is a view of the first step of the method of manufacture of the oximetry sensor of the present invention.

Referring to drawing FIG. 4, the first step in the manufacture of the oximetry sensor 10 is illustrated. The cable 22 is provided with a suitable connector 40 on one end thereof while the LED assembly 18 and the photodiode 20 are installed on the appropriate wires 24 of the cable 22 on the other end thereto, the cable 22, connector 40, wires 24, LED assembly 18, and photodiode 20 being reusable and capable of being sterilized using suitable, known sterilization procedures commonly available.

Figure 5:
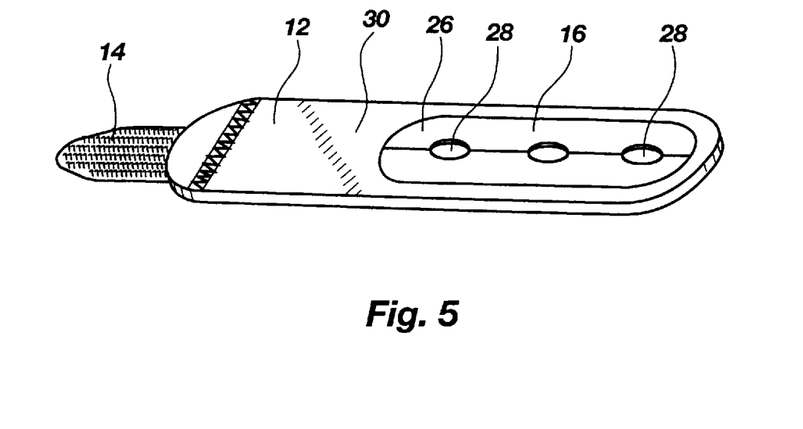
FIG. 5 is a view of the second step of the method of manufacture of the oximetry sensor of the present invention.

Referring to drawing FIG. 5, the wrap member 12 has adhesive member 16 installed thereon by the member 16 adhesively engaging the foam portion 30 of the wrap member 12 as the adhesive member 16 is formed having an adhesive coating on each side thereof. The adhesive member 16 contains a paper covering 26 thereon to be removed prior to the installation of the wrap member 12 on a patient. As shown, the adhesive member 16 is a rectangular shaped member which surrounds the apertures 28 in the wrap member 12 used to mount the LED assembly 18 and photodiode 20.

Figure 5A:
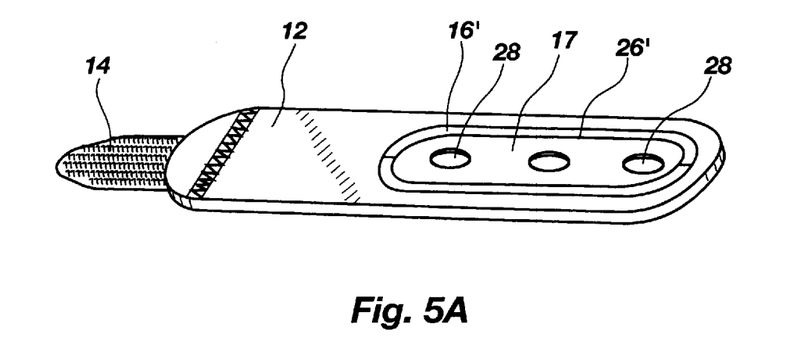
FIG. 5A is a view of an alternative adhesive wrap member for use in the present invention.

Referring to drawing FIG. 5A, an alternative embodiment of the adhesive member 16' is shown for use on the wrap member 12 of the oximetry sensor 10 of the present invention. The adhesive member 16' is an elongated, annular, rectangular shaped, double-sided, adhesively coated member having a central aperture 17 therein surrounding the apertures 28 in the wrap member 12 and having a removable covering 26', such as paper, thereover which is removed prior to the installation of the member 16' on the finger of a patient. Alternately, the adhesive member 16' may be a single-sided adhesive member adhesively secured to the wrap member 12 of a material, such as a soft, pliable, resilient elastomeric material, having sufficient friction with the finger of a patient to prevent movement of the wrap member 12 thereon during use.

Figure 6:
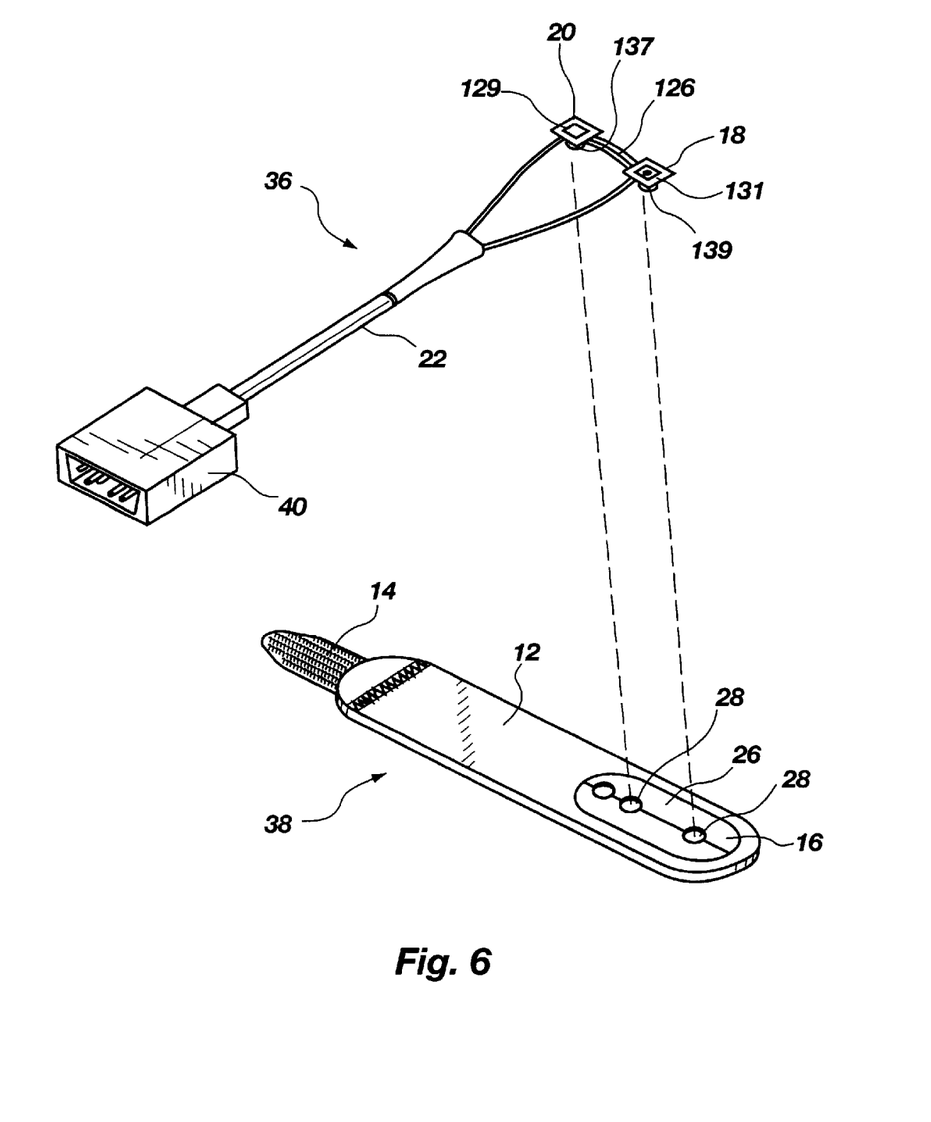
FIG. 6 is a view of the method of use of the oximetry sensor of the present invention.

Referring to drawing FIG. 6, the completed subassembly 36 is shown of the cable 22 having connector 40 on one end thereof and LED assembly 18 and photodiode 20 on the other end thereof. The completed subassembly 38 is shown of the wrap member 12 having adhesive member 16 having, in turn, covering 26 thereon being adhesively retained on the wrap member 12. The subassembly 36 is joined to the subassembly 38 by the flanges 137 and 139 of the photodiode 20 and LED assembly 18, respectively, being inserted into apertures 28 of the wrap member 12. In this manner, the subassembly 36 is securely mounted on the subassembly 38 in the desired position thereon by the flanges 137 and 139 engaging one side of the wrap member 12 while the flanges 129 and 131 of the photodiode 20 and LED assembly 18 respectively, engage the other side thereof.

Figure 7:
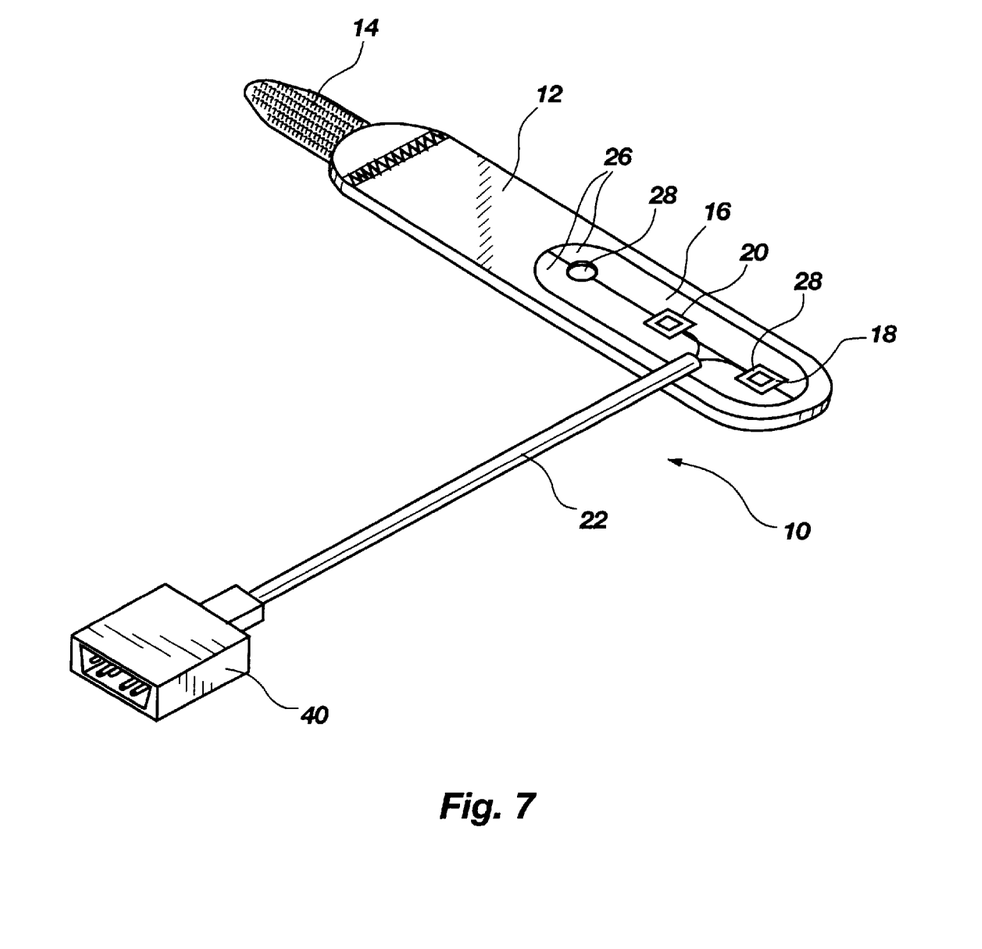
FIG. 7 is a view of the oximetry sensor of the present invention.

Referring to drawing FIG. 7, the oximetry sensor 10 of the present invention is shown in its assembled, completed form ready for use on a patient. The oximetry sensor including a wrap member 12 including a fastener 14, adhesive member 16 initially having a covering 26 thereover, LED assembly 18, and photodiode 20 connected to a cable 22 having connector 40 thereon.

From the foregoing, it is easily seen that the oximetry sensor 10 of the present invention offers any advantages over the prior art sensors. The oximetry sensor 10 is generally easily manufactured from inexpensive materials, is easy to use on a patient, is easy to reuse on a patient, and is comfortable in use on a patient. Since the oximetry sensor 10 of the present invention uses adhesive member 16 to attach the sensor 10 to a patient, the sensor 10 is quickly applied to a patient having adhesive contacting the skin of a patient to retain the sensor 10 in position without causing discomfort from the wrap member 12 being too tightly secured to the patient. The oximetry sensor 10 of the present invention is easily adjustable and has an extended life in comparison to solely adhesively retained sensors. The oximetry sensor 10 also is easy to reposition on a patient for optimum signal and comfort. Additionally, since the wrap member is conformable and compressive, the oximetry sensor may be easily repositioned on a patient without unwrapping the sensor from the patient while the adhesive member 16 retains the sensor in the desired position. The combination of the foam wrap and fabric back provides comfort to the patient and a readily conformable sensor. The foam wrap and fabric back also allow the sensor to breath and help minimize sweating of a patient. Since the oximetry sensor 10 of the present invention is not solely retained on the patient through the use of adhesives, the sensor is very suited to patients who may be sensitive or have allergies to adhesives. As previously stated, the sensor 10 is non-traumatic during use since it is conformable and compressible. Since the oximetry sensor 10 is simple to manufacture from relatively inexpensive materials, it is disposable but has a long life during use as compared to adhesive type sensors as well as being readily reusable on a patient. The oximetry sensor 10 of the present invention may be readily trimmed to customize the application of the sensor to a patient Additionally, the oximetry sensor 10 may be sterilized if so desired since the materials from which the sensor is made will accept sterilization.

It can be seen from the foregoing that changes, deletions and modifications to the oximetry sensor of the present invention may be made which fall within the scope of the invention. Additionally, it can be further seen from the foregoing that changes, additions, deletions and modifications to the method of manufacturing of the oximetry sensor of the present invention may be made which fall within the scope of the invention.

We claim:

1. An oximetry sensor comprising:
    a wrap member having a plurality of apertures therein, the
        wrap member including a compliant foam substrate and a fabric cover secured to at least a portion of the compliant foam substrate and extending over one side of the compliant foam substrate, wherein said plurality of apertures extend through said compliant foam substrate and said fabric cover, including a fastener secured to one end thereof, the fastener having a portion thereof engagable with a portion of the fabric cover of the wrap member, and including an adhesive member secured to another side of the compliant foam substrate and surrounding the plurality of apertures;

an LED assembly having a portion thereof engaging an aperture of the plurality of apertures in the wrap member; and a photodiode having a portion thereof engaging another aperture of the plurality of apertures.

2. The oximetry sensor of claim 1, wherein the adhesive member secured to the compliant foam substrate is adhesively secured thereto.

3. The oximetry sensor of claim 1, wherein the adhesive member secured to the wrap member is an annular shaped member.

4. The oximetry sensor of claim 1, wherein the adhesive member secured to the wrap member comprises a generally rectangular shaped member secured to the wrap member.

5. The oximetry sensor of claim 1, wherein the adhesive member secured to the wrap member includes a release liner thereover.

6. The oximetry sensor of claim 5, wherein the adhesive member secured to the wrap member includes a double sided adhesively coated member.

7. The oximetry sensor of claim 1, wherein the compliant foam substrate includes one of a polyester foam and a plastic foam substrate.

8. The oximetry sensor of claim 1, wherein the compliant foam substrate includes one of a polyester foam, a plastic foam, and a compliant foam substrate and the fabric cover comprises a cloth member.

9. The oximetry sensor of claim 1, further comprising: a cable connected to the LED assembly and the photodiode.

10. The oximetry sensor of claim 1, wherein fabric cover comprises a cloth member.

11. The oximetry sensor of claim 10, wherein the fastener of the wrap member includes a plurality of hooks thereon to engage the fabric cover of the wrap member.

12. The oximetry sensor of claim 11, wherein the fabric cover of the wrap member includes a plurality of loops therein to engage the plurality of hooks located on the fastener.

13. The oximetry sensor of claim 1, wherein the LED assembly and the photodiode are connected to a cable having a connector on one end thereof.

14. The oximetry sensor of claim 1, wherein the LED assembly and the photodiode each include a housing, each housing including an integral upper flange and an integral lower flange.

15. The oximetry sensor of claim 14, wherein the housing includes a cover therefore, the cover being transparent to infrared light.

16. A method of making an oximetry sensor, wherein the method comprises the steps of:

providing an LED assembly having a housing including two flanges thereon;

providing a photodiode having a housing including two flanges thereon;

providing a wrap member having a cloth cover, the wrap member including a compliant foam substrate, the cloth cover secured to at least a portion of the foam substrate and extending over one side of the compliant foam substrate, including a fastener secured to one end of the wrap member, the fastener having a portion thereof engageable with a portion of the cloth cover of the wrap member, an adhesive member secured to the wrap member having a removable liner cover thereover, and a plurality of apertures extending through the compliant foam substrate, the cloth cover, the adhesive member, and the removable liner cover of the wrap member;

inserting the photodiode within one of the plurality of apertures in the wrap member; and inserting the LED assembly within another aperture in the wrap member.

17. The method of claim 16, wherein the method includes the step of:

providing a cable;

attaching a portion of a cable to the photodiode; and attaching another portion of a cable to the LED assembly.

18. An oximetry sensor comprising:

a wrap member having a cloth cover, the wrap member including a compliant foam substrate, the cloth cover secured to at least a portion of the foam substrate and extending over one side of the compliant foam substrate, a fastener secured to one end of the wrap member, the fastener having a portion thereof engageable with a portion of the cloth cover of the wrap member, a plurality of apertures extending through the compliant foam substrate and the cloth cover, and an adhesive member surrounding the plurality of apertures; and a LED assembly and a photodiode, each secured in an aperture of the plurality of apertures in the wrap member.

19. The oximetry sensor of claim 18, wherein the compliant foam substrate comprises one of polyester foam and plastic foam.

20. The oximetry sensor of claim 19, wherein the fastener of the wrap member includes a plurality of hooks thereon to engage the cloth cover portion of the wrap member.

21. The oximetry sensor of claim 20, wherein the cloth cover portion of the wrap member includes a plurality of loops therein to engage the plurality of hooks located on the fastener.

22. The oximetry sensor of claim 20, wherein the adhesive member secured to the wrap member is adhesively secured thereto.

23. The oximetry sensor of claim 20, wherein the adhesive member secured to the wrap member comprises a generally rectangular shaped member secured to the wrap member.

24. The oximetry sensor of claim 20, wherein the adhesive member secured to the wrap member comprises a generally elongated in shape member secured to the wrap member.

25. The oximetry sensor of claim 20, wherein the adhesive member secured to the wrap member is annular in shape.

26. The oximetry sensor of claim 25, wherein the adhesive member secured to the wrap member includes a double sided adhesively coated member.

27. The oximetry sensor of claim 25, wherein the adhesive member secured to the wrap member includes an adhesive member having one side thereof adhesively coated.

28. The oximetry sensor of claim 20, wherein the adhesive member secured to the wrap member includes a release liner thereover.

29. The oximetry sensor of claim 20, wherein the adhesive member secured to the wrap member includes a member of silicon elastomer.

* * * * *

UNITED STATES PATENT AND TRADEMARK OFFICE
CERTIFICATE OF CORRECTION

PATENT NO. : 5,999,834
DATED : December 7, 1999
INVENTOR(S) : Wang et al.

It is certified that error appears in the above-identified patent and that said Letters Patent is hereby corrected as shown below:

Title page,
Item [54], after "MAKING" insert -- SAME --

Column 1,
Line 3, after "MAKING" insert -- SAME --;
Line 21, change "light emitting" to -- light-emitting --;
Line 27, change "light emitting" to -- light-emitting --;
Line 42, change "long term" to -- long-term --;

Column 2,
Line 1, after "lower" insert -- the --;
Line 31, after "sensor" insert -- . --;

Column 3,
Line 1, change "cover" to -- covering --;
Line 3, after "22" and before "." insert -- (see FIG. 1A) --;
Line 11, after "plastic foam" delete "," and after "substrate" (second occurrence) insert --, --
Line 35, after "the" insert -- adhesive --;
Line 48, after "the" insert -- adhesive --;
Line 51, after "retain the" insert -- adhesive --;
Line 57, change "light emitting" to -- light-emitting --;
Line 58, change "light emitting" to -- light-emitting --;

Column 4,
Line 4, change "opening" to -- aperture --;
Line 11, change "(FIG. 2)" to -- (FIG. 1A) --;
Line 27, after "material" insert -- and --;
Line 33, change "129" to -- 127 --;
Line 46, after "before" delete "the" at end of line;
Line 52, afte "such" insert -- as --;
Line 60, after "126" insert -- (not shown) --;

Column 5,
Line 21, after "member" insert -- 12 --;
Line 38, after "the" insert -- adhesive --;
Line 47, after "20" and before "." insert -- (not shown) --; and
Line 56, after "of the" insert -- adhesive --.

UNITED STATES PATENT AND TRADEMARK OFFICE
CERTIFICATE OF CORRECTION

PATENT NO.   : 5,999,834
DATED        : December 7, 1999
INVENTOR(S)  : Wang et al.

It is certified that error appears in the above-identified patent and that said Letters Patent is hereby corrected as shown below:

Column 7, claim 3,
Line 20, change "wrap member" to -- compliant foam substrate --;

Column 7, claim 4,
Line 23, change "wrap member" to -- compliant foam substrate --;
Line 24, change "wrap member" to -- compliant foam substrate --;

Column 7, claim 5,
Line 26, change "wrap member" to -- compliant foam substrate --;

Column 7, claim 6,
Line 29, change "wrap member" to -- compliant foam substrate --;
Lines 29-30, change double sided" to -- double-sided, --;

Column 7, claim 10,
Line 40, after "wherein" insert -- the --;

Column 7, claim 15,
Line 56, after "wherein" change "the" to -- each --;
Line 57, delete "therefore";

Column 7, claim 16,
Line 67, after "the" insert -- compliant --;

Column 8, claim 16,
Line 8, change "wrap" to -- adhesive --;
Line 11, after "aperture" insert -- of the plurality of apertures --;

UNITED STATES PATENT AND TRADEMARK OFFICE
CERTIFICATE OF CORRECTION

PATENT NO.   : 5,999,834
DATED        : December 7, 1999
INVENTOR(S)  : Wang et al.

It is certified that error appears in the above-identified patent and that said Letters Patent is hereby corrected as shown below:

Column 8, claim 17,
Line 14, change "step" to -- steps --;
Line 16, after "of" change "a" to -- the --;
Line 17, change "a" to -- the --;

Column 8, claim 18,
Line 21, after "of the" insert -- compliant --;
Line 28, after "member" insert -- secured to and --;
Line 30, change "a LED" to -- and LED --; and Column 8, claim 26,
Lines 55-56, change "double sided" to -- double-sided, --.

Signed and Sealed this

Eighth Day of January, 2002

*Attest:*

*Attesting Officer*

JAMES E. ROGAN
*Director of the United States Patent and Trademark Office*